United States Patent [19]

Derrien et al.

[11] 4,388,226

[45] Jun. 14, 1983

[54] PREPARATION OF MIXED OXIDE CATALYSTS COMPRISING THE OXIDES OF MOLYBDENUM AND/OR TUNGSTEN

[75] Inventors: Jean-Yves Derrien, Bourg-la-Reine; Paul Belon, Ales, both of France

[73] Assignee: Rhone-Poulenc Industries, Paris, France

[21] Appl. No.: 316,896

[22] Filed: Oct. 30, 1981

[30] Foreign Application Priority Data

Nov. 28, 1980 [FR] France .................................. 80 25261

[51] Int. Cl.$^3$ ......................... B01J 23/82; B01J 23/84; B01J 23/85; B01J 23/88
[52] U.S. Cl. ................................... 252/470; 252/465; 252/469
[58] Field of Search ......................... 252/465, 469, 470

[56] References Cited

U.S. PATENT DOCUMENTS 3,907,712 9/1975 Ohara et al. ..................... 252/470 X
4,166,808 9/1979 Daumas et al. .................. 252/455 R
4,224,187 9/1980 Vanderspurt .................... 252/470 X

*Primary Examiner*—W. J. Shine
*Attorney, Agent, or Firm*—Burns, Doane, Swecker & Mathis

[57] ABSTRACT

Mixed oxide active catalysts having the formula:

$A_a Mo_c W_d Co_e B_b O_x$ wherein:
A is at least one of the metals nickel, manganese and/or lead;
B is at least one of the metals iron, bismuth, chromium and/or thallium;
a is the sum of the values indicating the amounts present of each of the metals A, and is a number ranging from greater than or equal to 0 to about 4;
c and d are numbers each equal to or greater than 0 and ranging to 12, with the sum c+d being about 12;
e is a number ranging from about 8 to about 12;
b is the sum of the values indicating the amounts present of each of the metals B, and is a number ranging from greater than 0 to about 1.5 [(c+d)−(a+e)]; and
x is a number satisfying all unbalanced valences, are prepared by, in a first stage, intimately admixing in aqueous phase the salts of all metals to comprise such active catalyst, with the salts of molybdenum and/or tungsten being ammonium salts and at least one salt of at least one of the metals A and B being a nitrate; and, in a second stage, drying and calcining. In the process, the problems of ammonium nitrate formation are avoided by, in the first stage, acidifying an aqueous solution comprising the ammonium salts of molybdenum and/or tungsten to a pH ranging from about 0.5 to 3, separating the molybdic and/or tungstic acid precipitates which thereby form and preparing an aqueous suspension thereof, and then admixing therewith aqueous solutions of the metal salts of the remaining metals comprising the catalyst.

10 Claims, No Drawings

PREPARATION OF MIXED OXIDE CATALYSTS COMPRISING THE OXIDES OF MOLYBDENUM AND/OR TUNGSTEN

CROSS-REFERENCE TO RELATED APPLICATION

Derrien copending application, Ser. No. 310,399, filed Oct. 9, 1981, assigned to the assignee hereof.

BACKGROUND OF THE INVENTION

1. Field of the Invention

The present invention relates to the improved preparation of certain catalysts, and, more especially, to the improved preparation of catalysts based upon the oxides of molybdenum and/or tungsten.

2. Description of the Prior Art

Catalysts based upon the oxides of molybdenum and/or tungsten are per se known to the prior art. Same are useful, in particular, for the preparation of $\alpha,\beta$-unsaturated aldehydes by the oxidation of olefins in gaseous phase.

Thus, French Pat. No. 1,514,167 features certain catalysts for the preparation of unsaturated aldehydes via the air or oxygen oxidation of olefins, such as propylene and isopropylene, such catalysts having the following general formula:

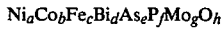

$$Ni_aCo_bFe_cBi_dAs_eP_fMo_gO_h$$

wherein a ranges from between 0 and 20, b between 0 and 20 (a+b being between 0.5 and 20), c between 0.5 and 8, d between 0.1 and 7, e between 0 and 3, with f being less than 0.1, g equal to approximately 12, and h being between 36 and 98.

These catalysts are prepared by adding an aqueous solution of suitable water soluble salts of nickel, cobalt, iron and bismuth, and a suitable compound of arsenic and of phosphorus, to an aqueous solution of a suitable molybdate, such as ammonium molybdate. The resultant slurry is heated, with a support if so desired, to eliminate the water and to dry the solid cake that is formed. The solid cake is then calcined in air, at an elevated temperature. The "suitable" water soluble salts noted in the aforementioned patent are nickel nitrate, cobalt nitrate, ferric nitrate and bismuth nitrate, for example.

French Pat. No. 1,604,942 relates to the preparation of acrolein, which consists of oxidizing propylene in gaseous phase, with a gas containing oxygen and water vapor, in the presence of a catalyst based upon the oxides of molybdenum, bismuth, iron and cobalt, and having the following elemental composition: Mo, 40 to 67.7%; Bi, 1.9 to 21.7%; Fe, 1.6 to 6.5% and Co, 21.0 to 48.1%.

The process for the preparation of these catalysts described in the above-cited patent consists of adding, to a vigorously agitated aqueous solution of ammonium molybdate, an aqueous solution of iron, cobalt and bismuth nitrate. Subsequently, the water is eliminated and the resultant product is calcined, optionally on a support.

Another prior art reference, French patent application No. 72/20810, published under No. 2,147,933, features a process for the preparation of unsaturated compounds having carbonyl functions from olefins. According to this particular process, the catalytic oxidation is effected in the presence of a catalytic oxide, wherein the atomic proportions of the elemental components Co/Fe/Bi/W/Mo/Si/Tl/Z (Z=alkali or alkaline earth metal) are 2.0 to 20.0/0.1 to 10.0/0.1 to 10.0/0.5 to 10.0/2.0 to 11.5/0.5 to 15.0/0.005 to 3.0/0 to 3.0, with the proviso that W+Mo is equal to 12.0.

And these particular catalysts may be prepared by mixing aqueous solutions of ammonium molybdate and of ammonium p-tungstate, by adding to the mixture aqueous solutions of cobalt nitrate, ferric nitrate, bismuth nitrate, thallium nitrate, together with the aqueous solution of a hydroxide or nitrate of an alkali or alkaline earth metal. Subsequently, the water is evaporated and the product obtained is calcined, optionally on a support.

There is also known to the prior art, in French patent application No. 76/27531, published under No. 2,364,061, a catalyst based upon the oxides of cobalt, molybdenum, bismuth and iron, having the formula: $Co_aMo_{12}Fe_bBi_cO_x$, with a being between 8 and 10, b between 0.5 and 2, c between 0.5 and 2 and x satisfying the valences, wherein the active phase contains a phase corresponding to the formula $Bi_2 Mo_2 Fe_2 O_{12}$. These catalysts make it possible to obtain, in very appreciably improved yields, $\alpha,\beta$-unsaturated aldehydes, for example, by oxidation of olefins.

These catalysts are prepared by reacting a solution of ammonium heptamolybdate and a solution of the nitrates of Co, Bi and Fe. The water is then evaporated and the resulting paste is dried. The solid obtained is subjected to an optional precalcination at approximately 450° C., a first calcination at a temperature between 450° C. and 500° C. for at least 5 hours, and then, after cooling in ambient air, to a second calcination under the same conditions as the first.

It will thus be appreciated that there exist a considerable number of references in the prior art describing the employment, in the oxidation of olefins (and particularly the oxidation of propylene to acrolein), of catalysts based principally upon the oxides of cobalt, iron, bismuth and molybdenum. A certain number of other oxides of metals too have been proposed as adjuvants to the base composition. It will also be appreciated that all of the processes for the preparation of these catalysts employ, in the first stage thereof, the reaction between ammonium heptamolybdate and the nitrates of iron, cobalt and bismuth.

During this reaction, ammonium nitrate is formed, which decomposes thermally at approximately 220° C. during subsequent calcination.

It is thus obvious that this thermal decomposition of ammonium nitrate poses serious practical and technical problems. In fact, those skilled in this art are very well aware that ammonium nitrate is an explosive compound and that, therefore, its handling on an industrial scale is quite dangerous.

It should also be emphasized that, in industrial practice, it is extremely difficult, if not impossible, to eliminate the simultaneous presence of ammonium salts and of nitrates.

Thus, serious need exists in the prior art for a process for the preparation of catalysts based, in particular, upon the oxides of molybdenum and/or tungsten, employing the reaction of at least one ammonium salt and at least one nitrate of the aforesaid metals, but wherein there is no danger, during the subsequent calcinations, of the thermal decomposition of ammonium nitrate.

Thus, serious need exists in the prior art for a process for the preparation of catalysts based, in particular, upon the oxides of molybdenum and/or tungsten, employing the reaction of at least one ammonium salt and at least one nitrate of the aforesaid metals, but wherein there is no danger, during the subsequent calcinations, of the thermal decomposition of ammonium nitrate.

SUMMARY OF THE INVENTION

Accordingly, a major object of the present invention is the provision of an improved process for the preparation of molybdenum/tungsten oxide catalysts devoid of those disadvantages and drawbacks to date plaguing the state of this art, which catalysts comprising an active phase having the general formula:

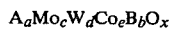

$$A_a Mo_c W_d Co_e B_b O_x$$

wherein:
(i) A represents at least one metal selected from the group comprising nickel, manganese, and lead;
(ii) B represents at least one metal selected from the group comprising iron, bismuth, chromium, and thallium;
(iii) a represents the sum of the indices assigned to each of the metals A; it is greater than or equal to 0 and less than or equal to approximately 4;
(iv) c and d are each greater than or equal to 0 and less than or equal to 12; with their sum c+d being equal to approximately 12;
(v) e is a number ranging from about 8 to about 12;
(vi) b represents the sum of indices assigned to each of the metals B; it is greater than 0 and less than or equal to approximately 1.5 [(c+d)−(a+e)]; and
(vii) x is a value satisfying the several valences; and the subject process comprising, in a first stage, in an aqueous phase, intermixing the salts of the metals entering into the final composition of the active phase, with the molybdenum and/or the tungsten being in the form of ammonium salts and at least one of the metals A and B being in the form of a nitrate; in a second stage, the resulting paste is dried; and, in a third stage, at least one calcination is effected upon the solids thus obtained, optionally while deposited on a support, said process being characterized in that, in the first stage, the first aqueous solution containing the ammonium salts of molybdenum and tungsten in amounts such as to obtain the desired values of c and d is acidified to such extent as to adjust the pH of the solution to a value ranging from approximately 0.5 to approximately 3; that, to the suspension which results, there is first added a second aqueous solution containing the salts of A and B in amounts such as to obtain the desired values of a and b, and serially thereafter cobalt carbonate is added thereto, in powder form, in such amount as to obtain the desired value of e; and that, the solution which thus results is evaporated to obtain the said second stage paste.

DETAILED DESCRIPTION OF THE INVENTION

More particularly according to this invention, a primary attribute thereof is that, when the aqueous solution containing the ammonium salts of molybdenum and/or tungsten is acidifed, molybdic and/or tungstic acid precipitates, while the ammonium ions remain in solution. Such ammonium ions are then removed by any suitable technique, for example, by filtration. When the ammonium ions are semi-quantitatively removed, there no longer exists any danger of the formation of ammonium nitrate in the downstream processing. But the suspension of the molybdic and/or tungstic acid is acidic (its pH ranging from about 1.5 to about 2). Thus, if the other metals (cobalt, A and B) are then added in nitrate form, the pH is again lowered, to a value which can even be less than 0.5. And at this pH, no satisfactory precipitation of metals ensues, especially of iron; the iron goes into solution with the molybdenum.

To obviate the immediately foregoing problem, the pH should be adjusted to a value on the order of about 2. It would of course be possible to add a pH-adjusting amount of ammonia, but then the problem of the formation of ammonium nitrate would reappear. However, it has now been determined that the major metal constituent other than the molybdenum and/or the tungsten, i.e., the cobalt, must be added in such form that will be decomposed by the acidity of the medium. And cobalt carbonate is admirably well suited for this purpose.

A granulometry of $70*10^{-6}$ to $1000*10^{-6}$ m is particularly well adapted to the invention.

As the ammonium salt that may be used in the process according to the invention, ammonium heptamolybdate is specifically mentioned. The latter may be used either in the form of crystallized ammonium heptamolybdate, or in the form of a mixture of ammonium dimolybdate and molybdic anhydride. When the first aqueous solution contains only ammonium heptamolybdate in one of the aforenoted forms, its pH is approximately 5.4

As the ammonium salt of tungsten, ammonium paratungstate is preferred.

When the first aqueous solution contains only ammonium paratungstate, its pH is approximately 5.8.

When a mixture of ammonium paratungstate and ammonium heptamolybdate is present, the pH varies from approximately 5.4 to 5.8, depending upon the relative proportions of the respective components.

The acidification of the first aqueous solution is effected with a relatively strong acid to adjust the pH to a value ranging from about 0.5 to approximately 3. It is also preferred that the acid have an anion that is easily thermally decomposed. Exemplary of such an acid is nitric acid.

According to one preferred embodiment of the invention, the first aqueous solution is acidified until a pH ranging from approximately 0.7 to approximately 1.5 is obtained.

According to another preferred embodiment of the invention, the pH of the suspension is adjusted to a value of approximately 2.

According to yet another preferred embodiment of the invention, there are employed a first aqueous solution exclusively containing ammonium heptamolybdate and a second aqueous solution containing no metal A, and as the metals B, iron, bismuth and cobalt carbonate, in amounts sufficient to obtain the desired catalytic formula, wherein e ranges from approximately 8 to approximately 10, c is equal to approximately 12 and b ranges from approximately 1 to approximately 4.

Even more preferably according to this invention, the immediately aforesaid solutions and the cobalt carbonate are utilized in amounts sufficient to provide a catalytic formula wherein e is equal to approximately 10, c is equal to approximately 12 and b is equal to approximately 2.

The different operations of the process according to the invention are preferably effected at ambient temperature.

The final evaporation is preferably carried out at a temperature ranging from 70° C. to 100° C.

The subsequent operations of drying and calcination(s), optionally while the catalyst is supported, are carried out consistent with known prior art techniques.

In order to further illustrate the present invention and the advantages thereof, the following specific examples are given, it being understood that same are intended only as illustrative and in nowise limitative.

EXAMPLE 1

Preparation of $Co_{10}Mo_{12}Fe_1Bi_1O_x$

A first aqueous solution of ammonium heptamolybdate was prepared by dissolving 167.6 g $(NH_4)_6Mo_7O_{24}.4H_2O$ in 760 cm³ $H_2O$ at ambient temperature. To this solution, maintained under agitation, a mixture of 72.5 cm³ $HNO_3$ having a density of 1.33 and 72.5 cm³ of $H_2O$ was added. The pH of the resulting solution was 0.8.

The mixture was filtered. A white crystalline solid consisting of molybdic acid was recovered (containing 93.8 g $MoO_3$).

The degree of precipitation of the molybdenum was 97%.

The $NH_4^+$ ions comprising the ammonium heptamolybdate were present in the filtrate in the form of ammonium nitrate. Analysis of the filtrate evidenced that all of the $NH_4^+$ ions were eliminated.

The precipitate was suspended in 600 ml water. The pH of the resultant suspension was 1.9.

A second aqueous solution was prepared by mixing together:
(i) 38.4 g of $Bi(NO_3)_3.5H_2O$ in 28.5 cm³ $H_2O$ acidified with 4.5 cm³ nitric acid; and
(ii) 32.1 g of $Fe(NO_3)_3.9H_2O$ in 25 cm³ $H_2O$.

This second solution was added to the aforesaid first suspension under agitation. The pH was then 0.6.

Thereafter, 94 g $CoCO_3$ were introduced, in powder form, under agitation.

The evolution of $CO_2$ was monitored. Upon completion of this addition, the pH was 3.4. Agitation was continued for 30 min.

Water was evaporated from the reaction mass, at 80° C., over the course of 3 hours. A paste which was non-flowing was obtained, which, following conventional processing according to typical prior art technique, yielded an optionally supported catalyst having the formula: $CO_{10}Me_{12}Fe_1Bi_1O_x$.

EXAMPLE 2

Preparation of $Co_8Mo_{12}Fe_{0.5}Bi_{0.5}O_x$

To the first aqueous solution obtained per Example 1, a mixture of 73 cm³ $HNO_3$ (density=1.33) and of 146 cm³ $H_2O$, was added. The resultant pH thereof was 1.3. The mixture was filtered; a white crystalline solid was recovered, consisting of molybdic acid containing 95.2 g $MoO_3$. The degree of molybdenum precipitation was 98.5%.

All of the $NH_4^+$ ions were present in the filtrate, in the form of ammonium nitrate.

The precipitate was suspended in 750 ml $H_2O$. The pH of the resultant suspension was 1.8.

A second aqueous solution was prepared by admixing:
(i) 19.2 g of $Bi(NO_3)_3.5 H_2O$ in 28.5 cm³ $H_2O$ acidified with 4.5 cm³ nitric acid; and
(ii) 16 g of $Fe(NO_3)_3.9 H_2O$ in 25 cm³ $H_2O$.

This second solution was added to the aforesaid first suspension under agitation. The pH was then 1.3.

Thereafter, 75.1 g cobalt carbonate in powder form were introduced thereto under agitation. The evolution of $CO_2$ was monitored. A paste which was non-flowing was obtained, which was then treated in conventional manner to yield a catalyst, optionally borne by a support, and having the formula:

$Co_8Mo_{12}Fe_{0.5}Bi_{0.5}O_x$

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a mixed oxide active catalyst having the formula:

$A_aMo_cW_dCo_eB_bO_x$ wherein:

A is at least one of the metals selected from nickel, manganese and lead;

B is at least one of the metals selected from iron, bismuth, chromium and thallium;

a is the sum of the values indicating the amounts present of each of the metals A, and is a number ranging from greater than or equal to 0 to about 4;

c and d are numbers each equal to or greater than 0 and ranging to 12, with the sum c+d being about 12;

e is a number ranging from about 8 to about 12;

b is the sum of the values indicating the amounts present of each of the metals B, and is a number ranging from greater than 0 to about 1.5 [(c+d)−(a+e)]; and x is a number satisfying all unbalanced valences, said process comprising, in a first stage, intimately admixing in aqueous phase the salts of all metals to comprise such active catalyst, with the salts of molybdenum and/or tungsten being ammonium salts and at least one salt of at least one of the metals A and B being a nitrate, and further wherein such first stage said intimate admixing comprises acidifying said first aqueous solution comprising said ammonium salts of molybdenum and/or tungsten in amounts sufficient to satisfy the values c and d to such extent as to adjust the pH thereof to a value ranging from about 0.5 to 3, separating the precipitate which forms thereby and forming an aqueous suspension thereof, next adding to said suspension a second aqueous solution comprising said A and B metal salts in amounts sufficient to satisfy the values a and b and, serially thereafter, also adding thereto cobalt carbonate, in powder form, in an amount sufficient to satisfy the value e, and thence concentrating the suspension which results to obtain a paste of the desired active catalyst; and, in a second stage, then drying said paste and, at least once, calcining same.

2. The process as defined by claim 1, wherein said first aqueous solution comprises only ammonium heptamolybdate.

3. The process as defined by claim 1, wherein said first aqueous solution comprises only ammonium paratungstate.

4. The process as defined by claim 1, wherein said first aqueous solution comprises a mixture of ammonium heptamolybdate and ammonium paratungstate.

5. The process as defined by claim 1, wherein said first aqueous solution is acidifed with nitric acid.

6. The process as defined by claim 1 or 5, wherein said first aqueous solution is acidifed to a pH ranging from about 0.7 to about 1.5.

7. The process as defined by claim 1, wherein the pH of the acidified suspension is about 2.

8. The process as defined by claim 1 or 2, wherein said first aqueous solution comprises ammonium heptamolybdate, and said second aqueous solution comprises no metal A, and as the metals B, iron and bismuth, with said solutions and cobalt carbonate being utilized in amounts such that e will range from about 8 to 10, b from about 1 to 4, and c will be about 12.

9. The process as defined in claim 8, wherein e will be about 10 and b about 2.

10. The process as defined by claim 1, wherein said active catalyst is calcined while borne by a support.

* * * * *